(12) United States Patent
Pratt et al.

(10) Patent No.: US 9,144,534 B2
(45) Date of Patent: Sep. 29, 2015

(54) AQUEOUS OXIDIZING COMPOSITION

(71) Applicant: KAO GERMANY GMBH, Darmstadt (DE)

(72) Inventors: Dominic Pratt, Groβ-Gerau (DE); Ovidiu Ferier-Iova, Darmstadt (DE)

(73) Assignee: KAO GERMANY GMBH, Darmstadt (DE)

(*) Notice: Subject to any disclaimer, the term of this patent is extended or adjusted under 35 U.S.C. 154(b) by 0 days.

(21) Appl. No.: 14/367,472

(22) PCT Filed: Dec. 20, 2012

(86) PCT No.: PCT/EP2012/076465
§ 371 (c)(1),
(2) Date: Jun. 20, 2014

(87) PCT Pub. No.: WO2013/092903
PCT Pub. Date: Jun. 27, 2013

(65) Prior Publication Data
US 2014/0335037 A1      Nov. 13, 2014

(30) Foreign Application Priority Data
Dec. 23, 2011   (EP) .................................... 11195612

(51) Int. Cl.
| | | |
|---|---|---|
| *A61K 8/22* | (2006.01) | |
| *A61K 8/41* | (2006.01) | |
| *A61K 8/42* | (2006.01) | |
| *A61K 8/92* | (2006.01) | |
| *A61K 8/19* | (2006.01) | |
| *A45D 7/04* | (2006.01) | |
| *A61Q 5/10* | (2006.01) | |
| *A61Q 5/08* | (2006.01) | |
| *A45D 7/00* | (2006.01) | |

(52) U.S. Cl.
CPC ... *A61K 8/22* (2013.01); *A45D 7/04* (2013.01); *A61K 8/19* (2013.01); *A61K 8/41* (2013.01); *A61K 8/42* (2013.01); *A61K 8/922* (2013.01); *A61Q 5/08* (2013.01); *A61Q 5/10* (2013.01); *A45D 2007/001* (2013.01)

(58) Field of Classification Search
USPC ............................... 8/504; 424/62, 70.5, 94.1
See application file for complete search history.

(56) References Cited

U.S. PATENT DOCUMENTS

| | | | | |
|---|---|---|---|---|
| 5,554,362 A | * | 9/1996 | Maresch et al. ............ | 424/70.51 |
| 7,341,715 B2 | * | 3/2008 | Dannecker et al. .......... | 424/70.5 |
| 2008/0075681 A1 | * | 3/2008 | Cassier et al. ............... | 424/70.2 |
| 2008/0075682 A1 | * | 3/2008 | Cassier et al. ............... | 424/70.2 |

FOREIGN PATENT DOCUMENTS

DE   EP0625350   *   3/1994 ............... A61K 7/09

* cited by examiner

*Primary Examiner* — Walter Webb
(74) *Attorney, Agent, or Firm* — Norris McLaughlin & Marcus PA

(57) ABSTRACT

Present invention relates to an aqueous oxidizing composition comprising at least one oxidizing, at least one alkyl or alkanol amine, urea, at least one carbonate salt and at least one natural triglyceride. Composition comprises furthermore hair dyes.

15 Claims, No Drawings

AQUEOUS OXIDIZING COMPOSITION

This application is a 371 application of PCT/EP2012/076465 filed Dec. 20, 2012, which claims foreign priority benefit under 35 U.S.C. §119 of European Application No. 11195612.4 filed Dec. 23, 2011, the disclosures of which are all incorporated herein by reference.

Present invention relates to an aqueous oxidizing composition comprising at least one oxidizing agent, at least one alkyl or alkanol amine, urea, at least one carbonate salt and at least one natural triglyceride.

Aqueous compositions comprising at least one oxidizing agent are widely being used either for lightening hair colour or adding additional colour to the existing hair colour or changing and/or achieving uniform appearance to hair. A successful colouration requires that hair to be coloured is homogeneously lightened in order to avoid any inhomogeneity in resulting hair colour. In other words, homogeneously lightened hair is coloured much more homogeneously than a hair comprising parts with different colour. This is especially the case for partially grayed hair and/or hair comprising streaks and/or comprising different colored highlights. Furthermore, hair comprising parts with various degree of damage is also difficult to colour and/or lighten.

Aim of the present invention is to provide an aqueous oxidizing composition for hair which lightens hair homogeneously and at the same time hair coloured with such compositions comprising additionally one or more hair dyes has much more homogeneous colour appearance. Aqueous composition of the present invention preferably does not comprise ammonia so that it does not have unpleasant smell.

Inventors of the present invention have surprisingly found out that an aqueous composition comprising at least one oxidizing agent, at least one alkyl or alkanol amine, urea, at least one carbonate salt and at least one natural triglyceride lightens hair homogeneously and an aqueous composition comprising additionally one or more hair dye colours hair homogeneously.

Accordingly, the first objective of the present invention is an aqueous composition for hair comprising at least one oxidizing agent, at least one alkyl or alkanol amine, urea, at least one carbonate salt and at least one natural triglyceride.

The second objective of the present invention is method of treating hair wherein an aqueous composition of the present invention is applied onto hair and after processing 1 to 45 min rinsed off from hair.

Compositions of the present invention are prepared prior to application onto hair by mixing two compositions wherein the first composition is an aqueous composition comprising at least one alkyl or alkanol amine, urea, at least one carbonate salt and at least one natural triglyceride and the second composition is an aqueous composition comprising at least one oxidizing agent. Accordingly further object of the present invention is method for treating hair wherein an aqueous composition comprising at least one alkyl or alkanol amine, urea, at least one carbonate salt and at least one natural triglyceride is mixed with an aqueous composition comprising at least one oxidizing agent immediately before use and applied onto hair and after processing 1 to 45 min rinsed off from hair.

Since compositions of the present invention is provided as two separate compositions to be mixed immediately before use, further object of the present invention is a kit for hair comprising two or more compositions wherein one of the compositions is an aqueous composition comprising at least one alkyl or alkanol amine, urea and at least one carbonate salt and another composition is an aqueous composition comprising at least one oxidizing agent.

Aqueous composition of the present invention comprises at least one oxidizing agent. Suitable ones are hydrogen peroxide, urea peroxide and melamine peroxide. The preferred oxidizing agent is hydrogen peroxide. Concentration of at least one oxidizing agent in the compositions of the present invention is in the range of 0.5 to 20%, preferably 1 to 15% and more preferably 2 to 12% by weight calculated to the total composition.

Aqueous composition of the present invention comprises at least one alkyl or alkanol amine. Preferably, at least one alkyl or alkanol amine is selected from the compounds according to general structure

wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is an alkyl or mono or polyhydroxyalkyl. More preferably at least one alkyl or alkanol amine is selected from the compounds according to above general structure wherein at least one of the $R_1$, $R_2$ and $R_3$ is a mono or polyhydroxyalkyl and further preferably $R_1$, $R_2$ and $R_3$ are same or different H, C1-C4 alkyl, C1-C4 monohydroxyalkyl or C2-C4 polyhydroxyalkyl with the condition that at least one of $R_1$, $R_2$ and $R_3$ is a mono or polyhydroxyalkyl. Most preferred embodiment of the present invention at least one alkyl oor alkanolamine is selected from compounds according to the above general formula wherein $R_1$, $R_2$ and $R_3$ are same or different H, C2-C4 alkyl, C2-C4 monohydroxyalkyl or C2-C4 polyhydroxyalkyl with the condition that at least one of $R_1$, $R_2$ and $R_3$ is a mono or polyhydroxyalkyl.

Suitable alkanolamines according to the general formula of above are monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

In a preferred embodiment of the resent invention the compositions are substantially free of ammonia and more preferably free of ammonia so that no disturbing ammonia smell is diffusing into the environment when using the compositions.

The concentration of at least one alkyl or alkanol amine in the compositions varies between 1 and 35%, preferably 1 and 30, more preferably 2.5 and 25 and most preferably 2.5 to 20% by weight calculated to the total composition.

The compositions of the present invention comprise urea preferably at a concentration of 1 to 15%, more preferably 1 to 10% and most preferably 1 to 7.5% and in particular 1.5 to 5% by weight calculated to the total composition.

Compositions of the present invention comprise at least one carbonate salt, preferably at a concentration of 0.2 to 10%, more preferably 0.5 to 10% and most preferably 0.5 to 5% and in particular 1 to 3% by weight calculated to the total composition.

Suitable carbonate salts are sodium, potassium, magnesium, guanidine and ammonium carbonates and bicarbonates. Preferred are sodium carbonate, sodium bicarbonate, ammonium carbonate, ammonium bicarbonate, guanidine carbonate and guanidine bicarbonate. More preferred are sodium, potassium ammonium and guanidine carbonates and the most preferred are sodium and ammonium carbonates. Particularly preferred carbonate salt is sodium carbonate.

Compositions of the present invention comprises urea and at least one alkyl or alkanol amine preferably at a weight ratio of at least 1.5, more preferably at least 1.6 and most preferably at least 1.75 and in particular at least 1.8.

Composition of the present invention comprises at least one natural triglyceride. Concentration of at least one natural triglyceride varies between 0.1 and 25%, preferably 1 and 25% and more preferably 3 and 20%, most preferably 5 and 20%, in particular 6 and 15% by weight calculated to the total composition.

Suitable ones are argan oil, shea butter oil, karite oil, olive oil, almond oil, avocado oil, *ricinus* oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, *passiflora* oil, black cumin oil, borage oils, grapeseed oil, hempseed oil, kukui nut oil, and rosehip oil. Preferred are argan oil, shea butter oil, karite oil, olive oil, almond oil, avocado oil, *ricinus* oil, coconut oil, palm oil, sesame oil, peanut oil, whale oil, sunflower oil, peach kernel oil, wheat germ oil, macadamia nut oil, macadamia oil, night primrose oil, jojoba oil, castor oil, and soya oil. More preferred are argan oil, shea butter oil, karite oil, macadamia nut oil, macadamia oil, olive oil, almond oil, avocado oil, *ricinus* oil, coconut oil, palm oil, sesame oil, peanut oil, sunflower oil, peach kernel oil, wheatgerm oil, jojoba oil, castor oil, and soya oil. Most preferred are argan oil, shea butter oil, karite oil, olive oil, almond oil, avocado oil, coconut oil, macadamia nut oil, macadamia oil, palm oil, sesame oil, peach kernel oil, wheatgerm oil, jojoba oil, and soya oil. Particularly preferred are argan oil, shea butter oil and karite oil which may be comprised as a single oil component or in admixture with each other.

Compositions of the present invention are used suitable for colouring hair. Coloring ompositions comprise at least one hair dye suitably selected from direct dyes and oxidative dye precursors and/or coupling agents. Suitable oxidative dyestuffs precursors are tetraaminopyrimidines, in particular 2,4,5,6-tetraaminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylenediamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene or the water-soluble salts thereof, pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts. The use of the above mentioned oxidative dye precursors as mixture is also customary in hair coloring area.

The total concentration of the oxidation dyestuff precursors and/or their water soluble salts customarily ranges between about 0.05% and 5%, preferably 0.1% and 4%, in particular 0.1% to 3% by weight, calculated to the total composition.

The composition according to the invention optionally comprises at least one coupling substance. Suitable ones are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hy-droxyethylamino)benzene, 1-amino-3-[bis(2'-hydroxy-ethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. However, this shall not exclude the addition of further developing and coupling substances. In the preferred embodiment of the present invention composition comprise additionally at least one coupling agent.

The weight proportion of the named developing substances to the coupling substances ranges between about 1:8 to 8:1, preferably about 1:5 to 5:1, in particular 1:2 to 2:1. In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition.

The composition of the present invention can comprise direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Orange 31, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 87 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), so called nitro dyes, are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

Further suitable direct dyes are according to the following structures.

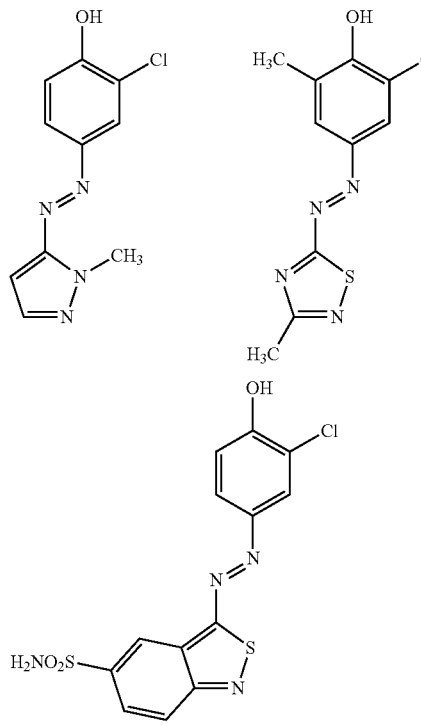

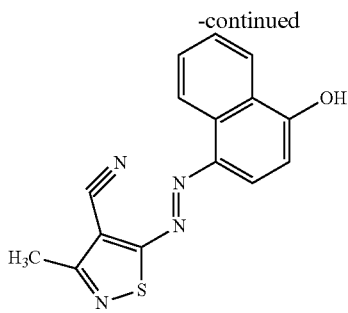

According to the invention, the composition comprises direct hair dyes at a total concentration of 0.01 to 5%, preferably 0.05 to 3%, more preferably 0.1 to 2% by weight calculated to total composition.

Compositions may further comprise additional substances found in lightening and/or coloring compositions for hair such as fatty alcohols, surfactants, gelling agents, emulsifiers, penetration enhancers, fragrance, humectants, conditioning agents, chelants and radical scavengers.

The compositions can comprise one or more fatty alcohol of the general formula $R_4$—OH wherein $R_4$ is a linear or branched, saturated or unsaturated alkyl chain with 12 to 22 C atoms. Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 1 to 25%, preferably 2.5 to 20%, more preferably 5 to 15% and most preferably 5 to 10% by weight calculated to total composition.

The composition of the present invention can comprise at least one surfactant, preferably selected from anionic, non-ionic, cationic and amphoteric surfactants. Preferred surfactants are anionic, non-ionic and cationic ones and especially preferred are the mixture of anionic and non-ionic surfactants and mixture of cationic non-ionic surfactants at any ratio. Preferred mixing ratio for the anionic-non-ionic surfactant mixture and cationic-non-ionic surfactant mixture is in the range of 5:1 to 1:5, more preferably 3:1 to 1:3 and especially 1:1, by weight. It should be noted that incompatibilities can arise when anionic and cationic surfactants are used as the mixture emulsifier which should be taken into account when selecting such a combination.

In principal any anionic surfactant is suitable within the meaning of the present invention. Nonlimiting examples are anionic surfactants of the sulfate, sulfonate, carboxylate and alkyl phosphate type, especially, of course, those customarily used as emulsifiers, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates and their salts.

Further suitable surfactants of the carboxylate type are alkyl polyether carboxylic acids and the salts thereof of the formula $R_5$—$(C_2H_4O)_n$—O—$CH_2COOX$, wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula $$R_{10}-\underset{\underset{O}{\|}}{C}-\underset{\underset{H}{|}}{N}-CH_2-CH_2-(C_2H_4O)_n-CH_2COOX$$

wherein $R_5$ and X have the above meanings, and n is in particular a number from 1 to 10, preferably 2.5 to 5.

Among the anionic surfactants most preferred are alkyl sulfates and/or alkyl ether sulfates and among them sodium lauryl or laureth sulfates and their mixtures are most preferred.

Suitable non-ionic surfactants are alkyl polyglucosides of the general formula $$R_6-O-(R_7O)_n O-Z_x$$

wherein $R_6$ is an alkyl group with 8 to 18 carbon atoms, $R_7$ is an ethylene or propylene group, Z is a saccharide group with 5 to 6 carbon atoms, n is a number from 0 to 10 and x is a number between 1 and 5. Examples are decyl polyglucoside and cocoyl polyglucoside, both being commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Among the non-ionic surfactants mentioned above fatty alcohol ethoxylates and fatty acid alkanolamides and their mixtures at any weight ratio are the most preferred ones.

As a rule any mono alkyl quaternary ammonium surfactants is suitable for the compositions of the present invention as cationic emulsifying surfactant. With the term mono alkyl it is meant that quaternary ammonium surfactant includes only 1 alkyl chain which has more than 8 C atoms. The term does not exclude that the quaternary ammonium surfactant includes further short alkyl chains, $C_1$ to $C_4$, present in the molecule.

Preferably at least one mono alkyl quaternary ammonium surfactant is selected from the compounds with the general formula $$R_{14}-\underset{\underset{R_{11}}{|}}{\overset{\overset{R_{12}}{|}}{N^+}}-R_{13} \quad X^-$$

where $R_{11}$ is saturated or unsaturated, branched or non-branched alkyl chain with 8-22 C atoms or $$R_{15}CONH(CH_2)_n$$

where $R_{15}$ is saturated or unsaturated, branched or non-branched alkyl chain with 7-21 C atoms and n has typical value of 0-4 or $$R_{16}COO(CH_2)_n$$

where $R_{16}$ is saturated or unsaturated, branched or non-branched alkyl chain with 7-21 C atoms and n has typical value of 0-4, and $R_{12}$, $R_{13}$ and $R_{14}$ are independent from each other lower alkyl chain with 1 to 4 carbon atoms, hydroxyl alky chain with 1 to 4 C atoms, or ethoxy or propoxy group with number of ethoxy or propoxy groups varying in the range of 1 to 4, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, behentrimonium chloride, trimethyl cetyl ammonium bromide, stearyl trimethyl ammonium chloride, stear trimonium chloride, stearamidopropyltrimethylammonium chloride, stearamidopropyl trimonuim chloride.

Surfactants are comprised in the compositions at a total concentration of 0.5 to 20%, preferably 1 to 15% and most preferably 2-10%, and most preferably 2 to 7.5% by weight, calculated to the total composition.

The compositions can comprise an organopolysiloxane wherein at least one silicon atom is linked to an alkylene group having a hetero-atom, in particular a nitrogen atom, with a poly-(N-acyl alkyleneimine) units of the formula $$-(CH_2)_n-\underset{\underset{C=O}{|}}{\overset{\overset{}{\|}}{N}}-$$
$$\quad\quad\quad R_{17}$$

wherein n is a number from 1 to 5 and $R_{17}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula $$CH_3-\left[\underset{\underset{(CH_2)_x}{|}}{\overset{\overset{CH_3}{|}}{Si}}O\right]_m\left[\underset{\underset{CH_3}{|}}{\overset{\overset{CH_3}{|}}{Si}}O\right]_n\underset{\underset{CH_3}{|}}{\overset{\overset{CH_3}{|}}{Si}}-CH_3$$
$$\quad\quad H_2N^{\oplus}+CH_2-CH_2-\underset{\underset{C_2H_5}{|}}{\overset{\overset{}{|}}{N}}+_y R_{18},$$
$$\quad\quad Y^{\ominus}\quad\quad\quad\quad\quad\quad\quad\quad C=O$$

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another compound that may be comprised in the compositions is a ceramide type of compounds according to the general formula

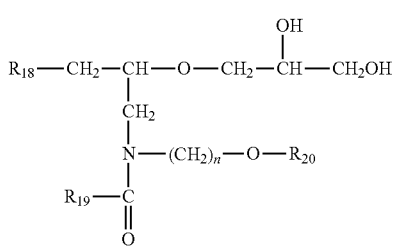

where $R_{18}$ and $R_{19}$ are independent from each other alkyl- or alkenyl group with 10 to 22 carbon atoms, $R_{20}$ is methyl, ethyl, n-propyl or isopropyl group and n is a number between 1 to 6, preferably 2 or 3. The concentration of the ceramide type of compound in colouring compositions of the present invention can be in the range of 0.01 to 2 and especially 0.01 to 1% by weight calculated to the total composition.

The compositions can further comprise one or more ubiquinone of the formula.

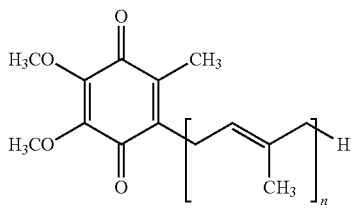

wherein n is a number from 1 to 10. The concentration of ubichinones in the compositions of the present invention can vary between 0.001% and 10% by weight, calculated to the total composition excluding the oxidizing agent.

Further, compositions can comprise yogurt powder at a concentration of 0.01 to 5% by weight calculated to total composition prior to mixing with oxidizing agent, which is a raw material prepared by spray drying of natural yoghurt after completion of fermentation. Yogurt powder comprises the following major components:
  approximately 53.5% lactose,
  approximately 25% proteins,
  approximately 7.5% lactic acid,
  approximately 5% minerals and trace elements,
  approximately 1% vitamines, and
  approximately 2% lipids.

Compositions of the present invention may further comprise any compound customarily found in such compositions such as organic solvents, complexing agent, fragrance, reducing agents, natural ingredients in the form of extracts or further active agents.

The following examples are used to illustrate the invention.

EXAMPLE 1

| | % by weght | | | | |
|---|---|---|---|---|---|
| | A | B | C | D | E |
| Hydrogen peroxide | 6.0 | 6.0 | 6.0 | 6.0 | 6.0 |
| Monoethanol amine | 3.9 | 3.9 | 3.9 | — | 3.9 |
| Ammonia | — | — | — | 3.9 | — |
| Urea | — | 5.0 | — | 3.3 | 3.3 |
| Sodium carbonate | — | — | 5.0 | 1.7 | 1.7 |
| Argan oil | — | — | — | 10.0 | 10.0 |
| Water | q.s. to 100 | | | | |

The above compositions were prepared by mixing all ingredients in water. pH of the all compositions were kept constant at 10.20. Hair streaks were lightened with the above compositions by applying above composition and processing at 40° C. for 30 min and washing with water. After drying hair streaks, L, a and b values were measured and ΔE values were calculated. The following data were obtained.

| Composition | ΔE |
|---|---|
| A | 6.7 |
| B | 7.1 |
| C | 7.3 |
| D | 7.2 |
| E | 9.8 |

It should be noted that the higher the ΔE value the more the lightening effect of the composition. From the above results the only conclusion may be drawn is that composition according to the present invention has the highest lightening effect.

EXAMPLE 2

| | % by weight |
|---|---|
| Hydrogen peroxide | 6.0 |
| Monoethanol amine | 6.8 |
| Urea | 3.3 |
| Sodium carbonate | 1.7 |
| Shea butter oil | 6.0 |
| Water | q.s. to 100 |

The above composition has an excellent lightening effect on hair.

EXAMPLE 3

| | % by weight |
|---|---|
| Octyldodecanol | 1.3 |
| Cetearyl alcohol | 1.0 |
| Oleyl alcohol | 2.6 |
| Argan oil | 7.0 |
| Ceteareth-20 | 1.0 |
| Sodium lauryl sulphate | 1.0 |
| Xanthan gum | 1.0 |

-continued

|  | % by weight |
| --- | --- |
| Sodium sulfit | 0.5 |
| Ascorbic acid | 0.2 |
| Tetrasodium EDTA | 0.2 |
| Fragrance, preservative | q.s |
| Monoethanolamine | 8.0 |
| Sodium carbonate | 2.5 |
| Urea | 6.0 |
| Water | q.s. to 100 |

Above composition had a pH of 11 and it was mixed with a composition comprising 12% hydrogen peroxide prior to application onto hair. The mixture had a pH of 9.5 and showed excellent lightening effect. The lightening performance was compared to a composition not comprising monoethanolamine, ammonium bicarbonate, urea and argan oil but having the same pH (adjusted with ammonia) showed considerably less lightening effect. Especially homogeneity of lightening effect was better with inventive composition compared to the comparative composition.

EXAMPLE 4

The composition of Example 3 was used as the base in the following examples.

| | Composition Number | | | | | |
| --- | --- | --- | --- | --- | --- | --- |
| Dyestuff | A | B | C | D | E | F |
| Toluene-2,5-diamine | 0.7 | 0.7 | — | 0.5 | — | 0.7 |
| p-Aminophenol | 0.1 | — | — | 0.5 | — | 0.1 |
| 1-Hydroxyethyl 4,5-Diamino Pyrazole Sulfate | — | 0.5 | — | — | — | — |
| Resorcinol | 0.05 | — | — | — | — | 0.05 |
| m-Aminophenol | 0.05 | — | — | — | — | 0.05 |
| 1-Naphthol | — | 0.9 | — | 0.5 | — | — |
| 4-Amino-2-hydroxytoluene | 0.1 | — | — | 0.5 | — | 0.1 |
| 2,4-Diaminophenoxyethanol | — | 0.01 | — | — | — | — |
| 2-Methylresorcinol | 0.01 | — | — | — | — | 0.01 |
| 1,3-Bis(2,4-diamino-phenoxy)propane | — | 0.01 | — | — | — | — |
| 2-Amino-4-Hydroxyethyl-Aminoanisole | — | 0.01 | — | — | — | — |
| 2-Amino-3-hydroxypyridine | 0.01 | — | — | — | — | 0.01 |
| Picramic Acid | — | — | 0.05 | — | — | 0.05 |
| Basic Red 51 | — | — | 0.5 | 0.7 | — | 0.5 |
| Basic Yellow 87 | — | — | 0.3 | 0.05 | — | 0.3 |
| Basic Orange 31 | — | — | 0.6 | 0.2 | — | 0.6 |
| 2-chloro-4[(E)-(1-methyl-1H-pyrazol-5-yl)diazenyl]phenol | — | — | — | — | 0.3 | 0.2 |
| 2,6-dimethyl-[(E)-(3-methyl-1,2,4-thiadiazol-5-yl)diazenyl]phenol | — | — | — | — | 0.7 | 0.7 |
| 3-[(E)-(3-chloro-4-hydroxyphenyl)diazenyl]-2,1-benzothiazole-5-sulfonamide | — | — | — | — | 0.2 | 0.01 |
| 5-[(E)-(4-hydroxynaphthalen-1-yl)diazenyl]-3-methyl-1,2-thiazole-4-carbonitrile | — | — | — | — | 0.1 | 0.01 |
| Color direction | Red | Violet | Orange | Red | Violet | Red |

The invention claimed is:

1. An aqueous composition for hair comprising at least one oxidizing agent, at least one alkyl or alkanol amine, urea, at least one carbonate salt and at least one natural triglyceride.

2. The composition according to claim 1 wherein the at least one oxidizing agent is hydrogen peroxide.

3. The composition according to claim 1 wherein the at least one alkyl or alkanolamine is selected from compounds according to general structure $R_1R_2R_3N$ wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is an alkyl or mono or polyhydroxyalkyl.

4. The composition according to claim 1 wherein the at least one alkyl or alkanol amine is present at a concentration of 1 to 35% by weight calculated to the total composition.

5. The composition according to claim 1 wherein the at least one alkyl or alkanolamine is monoethanolamine.

6. The composition according to claim 1 wherein the urea is present at a concentration 1 to 5% by weight, calculated to the total composition.

7. The composition according to claim 1 wherein the at least one carbonate salt is selected from sodium carbonate, sodium bicarbonate, ammonium carbonate, ammonium bicarbonate, guanidine carbonate and guanidine bicarbonate and their mixtures.

8. The composition according to claim 7 wherein the at least one carbonate salt is sodium carbonate.

9. The composition according to claim 1 wherein the carbonate salt is present at a concentration of 0.2 to 10% by weight calculated to the total composition.

10. The composition according to claim 1 wherein the urea and the at least one alkyl or alkanol amine are present at a weight ratio of 1.5 and higher.

11. The composition according to claim 1 wherein the at least one natural triglyceride is selected from argan oil, shea butter oil, karite oil, olive oil, almond oil, avocado oil, *ricinus* oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, *passiflora* oil, black cumin oil, borage oils, grapeseed oil, hempseed oil, kukui nut oil, and rosehip oil and is present in the concentration range between 0.1 and 25% by weight calculated to total composition.

12. The composition according to claim 1 wherein the composition is free of ammonia.

13. The composition according to claim 1 further comprising at least one hair dye selected from direct and oxidative dyes.

14. Method of treating hair wherein an aqueous composition comprising applying a composition according to claim 1 onto hair and after processing 1 to 45 min rinsed off from hair.

15. Kit for hair characterized in that it comprises two or more compositions wherein the first composition is an aqueous composition comprising at least one alkyl or alkanol amine, urea, at least one carbonate salt and at least one natural triglyceride and the second composition comprising at least one oxidizing agent.

* * * * *